US010470457B2

(12) United States Patent
Zhu et al.

(10) Patent No.: US 10,470,457 B2
(45) Date of Patent: Nov. 12, 2019

(54) METHOD OF CRYOPRESERVATION OF STEM CELL-DERIVED RETINAL PIGMENT EPITHELIAL CELLS ON POLYMERIC SUBSTRATE

(71) Applicant: University of Southern California, Los Angeles, CA (US)

(72) Inventors: Danhong Zhu, Covina, CA (US); David Hinton, Venice, CA (US); Ashish Ahuja, New York, NY (US); Mark Humayun, Glendale, CA (US)

(73) Assignee: University of Southern California, Los Angeles, CA (US)

( * ) Notice: Subject to any disclaimer, the term of this patent is extended or adjusted under 35 U.S.C. 154(b) by 262 days.

(21) Appl. No.: 15/418,099

(22) Filed: Jan. 27, 2017

(65) Prior Publication Data

US 2017/0196221 A1    Jul. 13, 2017

Related U.S. Application Data

(63) Continuation of application No. 14/114,182, filed as application No. PCT/US2012/035676 on Apr. 27, 2012, now abandoned.

(60) Provisional application No. 61/481,015, filed on Apr. 29, 2011.

(51) Int. Cl.
| | |
|---|---|
| A01N 1/02 | (2006.01) |
| A61L 27/16 | (2006.01) |
| A61L 27/34 | (2006.01) |
| A61L 27/38 | (2006.01) |
| A61L 27/58 | (2006.01) |
| C12N 5/079 | (2010.01) |

(52) U.S. Cl.
CPC ......... *A01N 1/0252* (2013.01); *A01N 1/0268* (2013.01); *A01N 1/0284* (2013.01); *A61L 27/16* (2013.01); *A61L 27/34* (2013.01); *A61L 27/3813* (2013.01); *A61L 27/3834* (2013.01); *A61L 27/58* (2013.01); *C12N 5/0621* (2013.01)

(58) Field of Classification Search
None
See application file for complete search history.

(56) References Cited

U.S. PATENT DOCUMENTS

| | | |
|---|---|---|
| 4,163,828 A | 8/1979 | Mahoney |
| 7,923,823 B2 | 4/2011 | Mengel |
| 8,877,489 B2 | 11/2014 | Tai et al. |
| 9,095,524 B2 | 8/2015 | Warnke et al. |
| 2003/0054331 A1 | 3/2003 | Fraser et al. |
| 2005/0106554 A1* | 5/2005 | Palecek ............... A01N 1/02 435/2 |
| 2009/0123992 A1 | 5/2009 | Chin |
| 2009/0130756 A1 | 5/2009 | Klann et al. |
| 2012/0009159 A1 | 1/2012 | Humayun et al. |
| 2013/0143326 A1 | 6/2013 | Tai et al. |
| 2014/0045264 A1 | 2/2014 | Zhu et al. |

FOREIGN PATENT DOCUMENTS

| | | |
|---|---|---|
| EP | 2702135 | 3/2014 |
| JP | 2003-047464 A | 2/2003 |
| JP | 2007-306856 A | 11/2007 |
| JP | 2014-512820 A | 5/2014 |
| WO | WO 2005/069766 A2 | 8/2005 |
| WO | WO 2007/058308 A1 | 5/2007 |
| WO | 2012/149484 A2 | 11/2012 |
| WO | WO 2012/149484 | 11/2012 |

OTHER PUBLICATIONS

Jinno et al, "Microfabricated multilayer parylene-C stencils for the generation of patterned dynamic co-cultures," Journal of Biomedical Materials Research Part A, Jul. 2008, pp. 278-288.
Lu et al, "Ultrathin Parylene-c semipermeable membranes for Biomedical Applications," 2011 IEEE 24$^{th}$ International Conference on Mircro Electro Mechanical Systems, MEMS 2011, pp. 505-508.
Teshima et al., "Paring single Adherent Cells in the Dynamic Microarray," 2011 IEEE 24$^{th}$ International Conference on Mircro Electro Mechanical Systems, MEMS 2011, pp. 71-74.
Katkov et al., "DMSO-Free Programmed Cryopreservation of Fully Dissociated and Adherent Human Induced Pluripotent Stem Cells," Stem Cells International, vol. 2011, Article ID 981606, 8 pages, 2011. doi: 10.4061/2011/981606.
Lu et al., Mesh-supported sub-micron parylene-C membranes for culturing retinal pigment epithelial cell, Biomed. Microdevices, vol. 14:659-667 (2012).
Amps, et al., In situ cryopreservation of human embryonic stem cells in gas-permeable membrane culture cassetts for high post-thaw yield and good manufacturing practice, Cryobiology, vol. 60. 344-350 (2010).
Li et al., Cryopreservation of Human Embryonic Stem Cells with a New Bulk Vitrification Method, Biology of Reproduction, vol. 82:848-853 (2010).
Nie et al., Scalable Culture and Cryopreservation of Human Embryonic Stem Cells on Microcarriers, Biotechnol. Prog., vol. 25(1): 20-31 (2009).
G.J. Morris, et al. "Cryopreservation of murine embryos, human spermatozoa and embryonic stem cells using a liquid nitrogen-free, controlled rate freezer." Reproductive BioMedicine Online, Jun. 23, 2006, vol. 13 (3), pp. 421-426, ISSN 1472-6483.
Nazare Pereira-Rodrigues, et al. "Modulation of hepatocarcinoma cell morphology and 24 lactivity by parylene-C coating on PDMS." In: PLoS ONE. Mar. 2010, vol. 5(3), p. e9667, ISSN 1932-6203.
Tracy Y. Chang, et al. "Cell and protein compatibilty of Parylene-C surfaces." In: Langmuir, 2007. vol. 23(23), pp. 11718-11725, ISSN 0743-7463.

* cited by examiner

*Primary Examiner* — Blaine Lankford
(74) *Attorney, Agent, or Firm* — Kilpatrick Townsend & Stockton LLP (57) ABSTRACT

Disclosed herein are methods and compositions for the cryopreservation of stem cells, such as stem-cell derived retinal pigment epithelial cells, that have been seeded onto and cultured on a substrate, such as a polymeric substrate. Such cryopreserved stem cells are useful for cell therapies, such as treatment of ocular damage or disease.

12 Claims, 3 Drawing Sheets

METHOD OF CRYOPRESERVATION OF STEM CELL-DERIVED RETINAL PIGMENT EPITHELIAL CELLS ON POLYMERIC SUBSTRATE

RELATED CASES

This application is a continuation of co-pending U.S. application Ser. No. 14/114,182, filed on Oct. 25, 2013, which is the National Phase under 35 U.S.C. § 371 of International Application No. PCT/US2012/035676, filed Apr. 27, 2012, which claims the benefit of U.S. Provisional Application Ser. No. 61/481,015, filed on Apr. 29, 2011, the contents of each of which is expressly incorporated in its entirety by reference herein.

BACKGROUND

Field of the Invention

The present application relates generally to methods and compositions for the cryopreservation of stem cells grown on a substrate. In particular, methods and compositions for the cryopreservation of retinal pigment epithelial (RPE) cells grown on a polymeric substrate.

Description of the Related Art

The scope of human disease that involves loss of or damage to cells is vast and includes, but is not limited to, ocular disease, neurodegenerative disease, endocrine diseases, cancers, and cardiovascular disease. Cellular therapy involves the use of cells, and in some cases stem cells, to treat diseased or damaged tissues. It is rapidly coming to the forefront of technologies that are poised to treat many diseases, in particular those that affect individuals who are non-responsive to traditional pharmacologic therapies.

In fact, many diseases that are candidates for application of cellular therapy are not fatal, but involve loss of normal physiological function. For example, ocular diseases often involve functional degeneration of various ocular tissues which affects the vision, and thus the quality of life of numerous individuals.

The mammalian eye is a specialized sensory organ capable of converting incoming photons focused by anterior optics (cornea and lens) into a neurochemical signal. This process of phototransduction allows for sight by sending action potentials to higher cortical centers via the optic nerve. The retina of the eye comprises photoreceptors that are sensitive to various levels of light and interneurons that relay signals from the photoreceptors to the retinal ganglion cells. These photoreceptors are the most metabolically active cells in the eye (if not the body), and are supported metabolically and functionally by retinal pigment epithelial cells (RPE). These RPE cells are positioned in a monolayer in the eye and are critical to vision.

Numerous pathologies can compromise or entirely eliminate an individual's ability to perceive visual images, including trauma to the eye, infection, degeneration, vascular irregularities, and inflammatory problems. The central portion of the retina is known as the macula, which is responsible for central vision, fine visualization and color differentiation. The function of the macula may be adversely affected by age related macular degeneration (wet or dry), diabetic macular edema, idiopathic choroidal neovascularization, high myopia macular degeneration, or advanced retinitis pigmentosa, among other pathologies.

Age related macular degeneration typically causes a loss of vision in the center of the visual field (the macula) because of damage to the retina. It is a major cause of visual impairment in older adults (>50 years). Macular degeneration occurs in "wet" and "dry" forms. In the dry form, cellular debris (drusen) accumulates between the retina and the choroid, which puts pressure on the retina, possibly leading to retinal detachment and loss of vision. In the more severe wet form, newly formed blood vessels from the choroid infiltrate the space behind the macula, which causes death of photoreceptors and their supporting cells. In conjunction with the loss of functional cells in the eye, the newly formed blood vessels are fragile and often leak blood and interstitial fluid, which can further damage the macula.

While diseases that cause damage to specific cells or tissues are clear candidates for cellular therapy, there remains a need in the art for improved methods of cellular therapy which includes methods, substrates, and tools to improve the efficacy of cellular therapy, as well as methods and compositions allowing for long term storage of functional and viable cells to be used in such therapies.

SUMMARY

To address the need for improved long term storage of cell-containing compositions for use in cell therapy, there is provided, in some embodiments, a method of cryopreserving stem cells on a substrate comprising exposing a substrate seeded with stem cells to a temperature ramp-down phase having a desired temperature reduction rate, transferring the cell-seeded substrate to a desired intermediate temperature range for a first period of time, and maintaining the stem cells at a desired storage temperature range for a second period of time, resulting in cryopreserved stem cells on a substrate that are suitable for long term storage and later use in cell therapy.

In several embodiments, the temperature ramp-down phase rate ranges from about 10° C. per 10 seconds to about 10° C. per 120 seconds temperature reduction. In other embodiments, greater or lesser rates may be used, depending, at least in part, on the type of cell to be cryopreserved, the substrate material, the dimensions of the substrate, and the durability of the cells (e.g., their sensitivity to rate of temperature change). In several embodiments, the desired intermediate temperature range is from about 0° C. to about −100° C., including from about 0° C. to about −10° C., about −10° C. to about −20° C., about −20° C. to about −30° C., about −30° C. to about −40° C., about −40° C. to about −50° C., about −50° C. to about −60° C., about −600° C. to about −70° C., about −70° C. to about −80° C., about −80° C. to about −90° C., about −90° C. to about −100° C., and overlapping ranges thereof. In several embodiments, the temperature ramp-down phase is adjusted such that the stem cell-seeded substrate reaches a temperature of around 0° C. This again depends, at least in part, on the cell type, the substrate, and the sensitivity of each to rate of temperature change. In several embodiments, the temperature reduction profile is tailored to maximize the similarity of response between the substrate and the cells. For example the temperature reduction profile, in some embodiments, is relatively shallow (e.g., smaller rate of reduction over time), to accommodate cells or substrate materials that are more sensitive to temperature changes. In such embodiments, the shallow reduction profile allows "acclimatization" of the cells/substrate to the serial reduction in temperature, which in several embodiments, leads to improved long-term storage, and increased viability and/or function after thawing.

The duration of storage at the intermediate temperature can range from short period of time (e.g., minutes to hours) to a longer duration (e.g., days to weeks). For example, in several embodiments, first period of time is between about 6 and 48 hours, such as for example, about 24 hours.

In several embodiments, the storage temperature is less than or equivalent to the intermediate temperature. In several embodiments, the storage temperature ranges from about −50° C. to about −60° C., about −600° C. to about −70° C., about −70° C. to about −80° C., about −80° C. to about −90° C., about −90° C. to about −100° C., and overlapping ranges thereof. In some embodiments, lower temperatures are used for the storage (e.g., maintenance) of the cryopreserved cells. In several embodiments, liquid nitrogen (or other similar liquid coolant) is used to store the cells. In several embodiments, the second period of time (e.g., the storage time) is greater than about 6 hours. In several embodiments, the second period of time is greater than about 72 hours. In several embodiments, the second period of time is about 48 hours to about one week.

In several embodiments, the substrate comprises parylene. In several embodiments, the substrate comprises parylene in combination with other materials, the other materials being either biodegradable or non-biodegradable. In several embodiments, the substrate is treated such that it has one or more characteristics that enhance viability of the seeded stem cells. For example, in several embodiments, substrate further comprises a coating to enhance adhesion of the stem cells to the substrate. In some embodiments, the coating comprises one or more of Matrigel, vitronectin, and retronectin. Other coatings or surface modifications are used in other embodiments, in order to achieve an improved cell adhesion to the substrate and/or improve the durability and/or viability of the cells during and after the cryopreservation process. For example, in several embodiments, the coating enhances the viability of the stem cells during cryopreservation, after cryopreservation, or both.

In some embodiments, the characteristics of the substrate comprise one or more of the coefficient of thermal expansion of the substrate, a substrate elasticity parameter, or a substrate thickness. In several embodiments, the substrate comprises parylene and is non-porous and permeable and the characteristic comprises substrate thickness, and the thickness is selected to allow nutrients to pass through the substrate. Thus, upon thawing and subsequent implantation at a target site, the substrate permits adequate nutrient passage to the cells and/or adequate passage of cellular waste material away from the substrate. In some embodiments, the thickness is selected to yield a thermal coefficient of expansion of the substrate such that has reduced adverse impact on the seeded cells.

In several embodiments, the seeded stem cells comprise hESC-RPE cells. In some such embodiments, the seeded stem cells comprise a monolayer of fully differentiated hESC-RPE cells. In several embodiments, the seeded stem cells comprise embryonic stem cells. In several embodiments, the seeded stem cells comprise adult stem cells. In several embodiments, the seeded stem cells comprise induced pluripotent stem cells. In additional embodiments, non-stem cells may optionally be used.

In several embodiments, in addition to cryopreserving stem cells, the methods disclosed herein further comprise thawing the cryopreserved stem cells on the substrate by a method comprising warming the cell-seeded substrate to a target temperature using a temperature ramp-up heating rate to obtain thawed stem cells seeded on the substrate, wherein the thawed stem cells retain viability and/or functionality post-thaw.

In several embodiments, the thawed stem cells are cultured in a media comprising growth supplements. In several embodiments, the growth supplements comprise one or more of fibroblast growth factor (FGF) and an FGF supplement. In some embodiments, no growth supplements are used.

In several embodiments, the thawed stem cells are suitable for direct implantation in an eye of a patient (e.g., without the need for subsequent culturing).

In several embodiments, there is also provided a method of cryopreserving stem cells, the method comprising cooling stem cells seeded on a parylene substrate using a temperature ramp-down phase having a pre-determined ramp-down cooling rate, transferring the seeded stem cells to an intermediate storing temperature; and maintaining the stem cells within a long-term storage temperature range for a predetermined period of time to thereby obtain cryopreserved stem cells, wherein the seeded stem cells maintain their viability after they are thawed.

In several embodiments, the predetermined ramp-down cooling rate comprises a rate of reduction in temperature of no more than about 20° C. per minute. In some embodiments, the predetermined ramp-down cooling rate comprises a rate of temperature reduction that is within a range of about 7° C. per minute to about 17° C. per minute. In several embodiments, the predetermined ramp-down cooling rate comprises a rate of temperature reduction that is within a range of about 10° C. per 10 seconds to about 10° C. per 200 seconds.

Additionally, there is provided an alternative method of cryopreserving stem cells, the method comprising freezing a stem cell-seeded substrate using a flash-freeze temperature ramp-down phase, the substrate comprising a polymer, transferring the seeded stem cells to a storage temperature; thereby obtaining cryopreserved stem cells. In several embodiments, the polymer comprises a biodegradable polymer. In several embodiments, the polymer comprises a non-biodegradable polymer.

In several embodiments there is also provided a method of cryopreserving cells, the method comprising exposing cells seeded on a substrate to a reduced temperature environment, wherein the reduced temperature environment is sufficient to freeze the cells and the substrate, wherein the substrate is non-porous and permeable; and transferring, after the exposure, the cell-seeded substrate to a temperature between about 0° C. to about −100° C., thereby obtaining cryopreserved cells.

BRIEF DESCRIPTION OF THE DRAWINGS

FIGS. 3A-3F depicts cell post-thaw cell viability.

DETAILED DESCRIPTION

Cell therapy, the introduction of new cells into a tissue in order to treat a disease, represents a possible method for repairing or replacing diseased tissue with healthy tissue. Many approaches involve administration of cells (e.g., stem cells) to a target tissue, which often yields low retention rates and decreased incidence of long-term persistence of the transplanted (or implanted) cells. This may be due to a variety of factors, including cell washout (from the target tissue) and/or low cell survival rates in the delivery media (or the target tissue). However, some diseases do not require the engraftment of complete integration of the delivered cells per se, but rather require growth factors, chemical signals, or other interactions with the delivered cells. Treatment of such diseases may be accomplished by the delivery of cells to a target tissue. In some therapies, the delivered cells are first grown on and then subsequently delivered while on a bio-compatible substrate. Several embodiments of the methods disclosed herein relate to the cryopreservation of such cell-seeded implants, such that they can be stored long-term and used for effective cell therapy at a later time. Advantageously, the disclosed methods allow for the preparation of an "off the shelf" therapeutic product, in which a surgeon identifies, from a plurality of cell-seeded and cryopreserved substrates, an optimal substrate for implantation into the target tissue of a patient. This obviates the need for long intermediate periods of time from the discovery of an illness (or presentation of symptoms, or injury) which other cell therapy approaches require in order to grow sufficient quantities of cells to provide therapeutic effect.

Several embodiments of the methods described herein enable cryopreservation of cells seeded on substrates for the long-term storage and scale up in large-scale production. As opposed to individual preparations of substrate-seeded cells, large scale production of substrate-seeded cells facilitates quality control and ease of use.

Embryonic and induced pluripotent stem cells represent potentially unlimited sources of differentiated cells for cell replacement therapy. Stem cell-derived retinal pigment epithelial cells (RPE) are one source for therapeutic cells for cellular therapy of the late form of atrophic age related macular degeneration (AMD). RPE cells function as differentiated, polarized monolayers. Successful cryopreservation of stem cell-derived differentiated and polarized RPE monolayers is beneficial for uniformity of a clinical product, maximization of product yield, assurance of quality control within a clinical product lot, and distribution of a similar final product to remote clinical sites. Scale-up that is in accordance with clinical good manufacturing (cGMP) and tissue practice (GTP) standards requires lot and final release testing that is practical for a manufacturer. While the cryogenic process of freezing and thawing is currently used for adult, umbilical cord blood, and pluripotent embryonic derived stem cell lines, and unpolarized embryonic stem cell derived RPE (hESC-RPE), Applicant is unaware to date of any other successful the preservation of polarized hESC-RPE-derived monolayers seeded on biocompatible substrates (as disclosed herein). Primary obstacles that, absent the methods disclosed herein, have not been overcome are reduction of survival and yield and the inability of derived RPE to adhere to polymeric substrates required for delivery of a polarized monolayer of cells. Thus, several embodiments of the present invention solve this long-felt need for functional, viable, and control-tested cells grown on, preserved on (and ready for subsequent implantation on) substrates.

Substrates

In several embodiments, cryopreservation of cells on an implantable substrate improves several aspects of cellular therapy. As used herein, the terms "substrate" shall be given its ordinary meaning and shall also be used interchangeably with the term "implant" and/or "device", though it shall be appreciated that some embodiments described herein do not require implantation per se (e.g., those functioning as a "patch on a target tissue surface").

A variety of different types of substrates may be used to treat various diseases, and as such may be subjected to the cryopreservation methods disclosed herein. For example, substrates may, in some embodiments, be three dimensional, flat, substantially planar, or of other dimensions, shapes, sizes or characteristics as may be appropriate. As used herein, the terms "3-dimensional" and "3-D" shall be given their ordinary meanings and are inclusive of devices resembling a cage (e.g., having one or more interior lumens or cavities). In light of such variability in the design of substrates disclosed herein, the disclosure below, unless otherwise specified shall be appreciated to be applicable to any such variety of substrate. Moreover, in light of the flexibility of several embodiments of the methods disclosed herein, the dimensions, shapes, number (e.g., single or plurality of joined or plurality of separated substrates) do not limit the applicability of the methods. For example, substrates seeded with stem cells to treat a large tissue area (e.g., an osteopathic graft) may be cryopreserved according to the methods disclosed herein as readily as substrates seeded with stem cells to treat a microscopic tissue area (e.g., a substrate to treat macular degeneration which may have, for example dimensions ranging from about 1 to about 15 mm and thicknesses ranging from about 1 to about 15 mm). It shall be appreciated that, in some embodiments, certain characteristics of the substrate (e.g., pore diameters and density (if the substrate has pores), substrate material, substrate thickness, substrate permeability, and the like) may affect the thermodynamic properties of the substrate. Moreover, depending on the embodiment these same characteristics may be tailored for the function of the implant. Thus, in some embodiments, selection and/or adjustment of parameters such as substrate diameter, length, width, thickness, porosity (if the substrate has pores) and the formulation of materials comprising the substrate can be adjusted to tailor the thermodynamic properties of the substrate. Additionally, the temperature ramp profile (e.g., its rate of temperature change and physical reaction to increases or decreases in temperature) of a particular substrate due to its material, thickness, porosity, permeability etc., is readily discerned by one of ordinary skill in the art without undue experimentation.

In several embodiments the cell-seeded substrate that is cryopreserved comprises a porous substrate. In several embodiments, the substrate is non-porous, while in still additional embodiments, substrate is non-porous and permeable. In several embodiments, the permeability of the substrate is defined, at least in part, by its dimensions (e.g., its thickness) rather than by way of any purposefully created pores or passageways through the substrate material. In some embodiments, such non-porous and permeable substrates comprise parylene. In several embodiments the substrate is biodegradable while in other embodiments, it is non-biodegradable. In some embodiments, the substrate comprises a combination of biodegradable and non-biodegradable portions. By way of example, in one embodiment in which the substrate is biodegradable, the substrate comprises a PLGA co-polymer. In such embodiments, the rate of biodegradation of the PLGA copolymer is controlled by varying the ratio of lactic acid to glycolic acid units in the copolymer. Some embodiments comprise a non-biodegradable material combined with a biodegradable material, the latter which may provide, for example, additional structural and mechanical support aiding in substrate handling during cell seeding and culturing and/or during surgical insertion into a tissue (e.g., the subretinal space). The material may also, in some embodiments, be used to add mass to the substrate to assist in handling during cell seeding and culturing and/or during surgical insertion into a tissue and/or to assist in orientation of the substrate. The substrates may be formed of metals, polymers, plastics, or combinations thereof. In some embodiments, the material allows the substrate to have sufficient elasticity, flexibility and potential elongation to not only conform to the target anatomy during and after implantation, but also remain unkinked, untorn, and undamaged during and after implantation. Some embodiments of the substrate comprise surface modification to improve performance of the cell seeded substrate, such as to promote cell viability and attachment of cells to the substrate. For example, surface modification may be achieved by functionalizing the surface. In some embodiments, functionalizing a substrate surface may be achieved by applying a coating to the surface of the substrate, or through any other suitable method. In several embodiments, functionalization of the surface provides improved cell adherence to the surface which, in several embodiments, improves the growth of cells seeded on the substrate and/or enhances the viability of the cells during and after the cryopreservation process. Illustrative examples of suitable materials for the substrate include parylene polypropylene, polyimide, glass, nitinol, polyvinyl alcohol, polyvinyl pyrolidone, collagen, chemically-treated collagen, polyethersulfone (PES), poly(glycerol-sebacate) PGS, poly(styrene-isobutyl-styrene), polyurethane, ethyl vinyl acetate (EVA), polyetherether ketone (PEEK), Kynar (Polyvinylidene Fluoride; PVDF), Polytetrafluoroethylene (PTFE), Polymethylmethacrylate (PMMA), Pebax, acrylic, polyolefin, polydimethylsiloxane (PDMS) and other silicone elastomers, polypropylene, hydroxyapetite, titanium, gold, silver, platinum, other metals and alloys, ceramics, plastics and mixtures or combinations thereof. Additional suitable materials used to construct certain embodiments of the substrates include, but are not limited to, poly-para-xylylenes (e.g., parylene, including but not limited to parylene A, parylene AM, parylene C, ammonia treated parylene, parylene C treated with polydopamine), poly(lactic acid) (PLA), polyethylene-vinyl acetate, poly(lactic-co-glycolic acid) (PLGA), poly(D,L-lactide), poly(D,L-lactide-co-trimethylene carbonate), collagen, heparinized collagen, denatured collagen, modified collagen (e.g., silicone with gelatin), other cell growth matrices (such as SYNTHEMAX™), poly(caprolactone), poly(glycolic acid), and/or other polymer, copolymers, or block co-polymers, poly(caprolactone) containing cyclic Arginine-Glycine-Asparagine, cyclic or linear Arginine-Glycine-aspartic acid, blends of polycaprolactone and polyethylene glycol (PCL-PEG), thermoplastic polyurethanes, silicone-modified polyether urethanes, poly(carbonate urethane), or polyimide. Thermoplastic polyurethanes are polymers or copolymers which may comprise aliphatic polyurethanes, aromatic polyurethanes, polyurethane hydrogel-forming materials, hydrophilic polyurethanes, or combinations thereof. Non-limiting examples include elasthane (poly(ether urethane)) such as Elasthane™ 80A, Lubrizol, Tecophilic™, Pellethane™, Carbothane™, Tecothane™, Tecoplast™, and Estane™. Silicone-modified polyether urethanes may include Carbosil™ 20 or Pursil™ 20 80A, and the like. Poly(carbonate urethane) may include Bionate™ 80A or similar polymers. Moreover, in several embodiments the substrate (and/or the cells) comprises materials (or chemicals) that allow for visualization of the substrate in situ, which are unaffected by the cryopreservation (and thawing) of the substrate and cells. Additional non-limiting embodiments of suitable substrates can be found in U.S. Provisional Application No. 61/363,630, filed Jul. 12, 2010, and in provisional applications identified by the following, filed Apr. 29, 2011, Appl. No. 61/481,004; and filed Apr. 29, 2011, Appl. No. 61/481,037, the entirety of each of which is incorporated herein by reference.

Furthermore, in several embodiments, a plurality of individual substrates is fabricated from a single, larger substrate frame using, for example, photolithographic techniques, injection molding, and the like. Cells can thereafter be seeded onto the individual substrates within the frame, and processed according to the cryopreservation methods disclosed herein. In other embodiments, single substrates are cryopreserved.

Cell Types

Cryopreserved stem cells on substrates are useful for the treatment of a variety of diseases. For example, in several embodiments, ocular cells are used to treat ocular diseases including, but not limited to age related macular degeneration (wet or dry), diabetic macular edema, idiopathic choroidal neovascularization, or high myopia macular degeneration. In some ocular embodiments, RPE cells are used. In several embodiments, cardiac stem cells are used to treat cardiovascular disorders such as myocardial infarction, ischemic cardiac tissue damage, congestive heart failure, aneurysm, atherosclerosis-induced events, cerebrovascular accident (stroke), and coronary artery disease. In several embodiments, liver stem cells are used to treat liver disease such as hepatitis, cirrhosis, cancer, and the like. Diseases in other tissues, such as the kidney, lung, pancreas, intestine, bone and/or cartilage, and neural tissues, among others, may be treated with the methods and devices disclosed herein. In some embodiments, harvested bone marrow stem cells may be used to repopulate hematopoietic cells that are reduced due to leukemias, cancers, or therapies that reduce blood cell counts.

Given the wide variety of diseases that induce cell damage or cell death, a wide variety of cell types can be seeded into or onto substrates described herein to achieve therapeutic effects. In some embodiments, cultured cells are used. In several embodiments, banked cells are used. In some embodiments, the cultured cells comprise stem cells. Stem cells are pluripotent cells capable of differentiating into a variety of different cell types. In some embodiments, embryonic stem cells are used, while in other embodiments, adult stem cells are used. In several embodiments, the embryonic stem cells are human embryonic stem cells. Embryonic stem cells, which are typically derived from an early stage embryo, have the potential to develop into any type of cell in the body. In some embodiments, H1, H7, H9, SHEF-1, or other similar FDA-approved stem cell lines are used. In several embodiments, the embryonic stem cells are obtained without destruction of the embryo. Adult stem cells are typically multipotent and can develop into a more limited number of cell types, typically those that are related to the tissue type from which the cells were isolated. In some embodiments, the stem cells are allogeneic to the recipient (e.g., as is the case with certain embryonic stem cells). In some embodiments, the stem cells are autologous to the recipient. In other embodiments, syngeneic cells are used, while in still other embodiments, xenogeneic cells are used. In some embodiments, freshly isolated cells are cultured and deployed into or onto the substrate for implantation into a recipient individual. In other embodiments, previously cryopreserved cells are used (e.g., banked cells that are seeded onto substrates and cryopreserved as disclosed herein). In some embodiments, induced pluripotent stem cells are used. In some embodiments, fetal, umbilical cord, placenta-derived, adult, induced, or human embryonic stem cells and/or their partially or fully differentiated cellular derivatives are used. Several embodiments employ retinal pigment epithelial (RPE) cells, mixtures of RPE and photoreceptors, hESC-RPE cells, Müller glial cells, ganglion cells, mixtures of Müller glial cells and ganglion cells, corneal endothelial cells, mixtures of corneal endothelial cells and collagen, corneal epithelial cells, mixtures of corneal epithelial cells and collagen, endothelial cells, pericytes, and/or mixtures of endothelial cells and pericytes.

Methods of Cryopreservation

Current methods of cryopreservation are often performed on cell suspensions of undifferentiated embryonic stem cells. Methods of freezing suspensions of many cell types (e.g., hESC-RPE) are unsuitable for cryopreservation of the same stem cells when grown on a substrate. In many cases, this is due to the required presence of high concentrations of mammalian serum (e.g., fetal bovine serum). Paradoxically, Applicant has discovered that the very substance that aids in the freezing of suspension cells adversely affects the ability of such cells to adhere to a substrate surface. Therefore, in several embodiments, the conditions of cryopreservation are optimized to preserve cell adhesion to the substrate, which advantageously improves not only the survival of the cells, but also the therapeutic efficacy of the cells on the substrate.

In several embodiments, stability of hESC-RPE transplants is improved by seeding highly differentiated (or completely) hESC-RPE on polymeric substrates (such as those disclosed above) and allowing the cells to form a polarized monolayer. Advantageously, cryopreservation at this stage represents a final clinical product that functions like a normal RPE monolayer. In some embodiments, methods described herein enable therapeutic use of cryopreserved cell seeded substrates with substantially no additional manipulation or alteration of the cells on the substrate. A surgeon can simply select one or more cell-seeded implants that have been thawed and proceed to implant them without delay. In some embodiments, the seeded cells are hESC-RPE cells. Several embodiments are directed to the cryopreservation of substrate-seeded hESC-RPE cells from the H9 ESC cell line.

In several embodiments, substrate-adhered hESC-RPE cells are frozen (without adverse effects on adherence, function or viability) for approximately 1-5 hours, 5-12 hours, 12-24 hours, 24-48 hours, 48 hours to one week, one week to two weeks, two to three weeks, three to four weeks or longer, and overlapping ranges thereof. In some embodiments, cell-seeded substrates are cryopreserved and stored for more than one month, for more than one year, or longer. In some embodiments, cryopreserved cells are grown on parylene substrate. In some embodiments, cryopreserved cells grown on a parylene substrate are implanted in the subretinal space, or in any other suitable target implantation site, of a subject after controlled thawing.

In some embodiments, a substrate comprises parameters selected to improve the integrity or functionality of cells adhered on the substrate. Characteristics of a substrate may be selected such that cells adhered on the substrate substantially maintain integrity or functionality post cryopreservation. For example, characteristics of a substrate may affect the thermodynamic properties of the substrate and may be tailored for the function of the implant. In some embodiments, selection and/or adjustment of parameters such as substrate diameter, length, width, thickness, density, porosity (of porous substrates) and the formulation of substrate materials are adjusted to tailor the thermodynamic properties of the substrate (e.g., the coefficients of thermal expansion and elasticity) to optimize the cryopreservation of stem cells grown on a substrate. In some embodiments, parameters of a substrate are optimized such that temperature ramp-up and ramp-down rates do not disrupt the integrity of the cellular monolayer and does not adversely affect the viability or function of the cells post-thaw. Moreover, in several embodiments, physical distortion of the substrate due to temperature changes is reduced (again, in order to reduce the disruption of cell adherence to the substrate and/or post-thaw cell viability). For example, disruption of tight-junctions between adjacent RPE cells by adherence to, and expansion or contraction of the polymeric substrate may negatively affect cell viability post-thaw. In some embodiments, a substrate may comprise a polymer material having parameters such as the coefficient of thermal expansion and elasticity, and specifications, such as geometry and thickness, that are controlled to optimize the cryopreservation (and viability of cells post-thaw) of stem cells grown on a substrate. In some embodiments, one or more selected parameters of a substrate enable substantially intact cell monolayers post thawing of the substrate.

Additionally, the methods disclosed herein are advantageous because cryopreservation of cell-seeded substrates facilitates development of a therapeutic by allowing for a cGMP-compliant transport of a final product to the clinical site, or operating room without risk of disrupting monolayer integrity. In some embodiments, cryopreserved cells seeded on a substrate are directly used as a therapeutic agent post-thaw. Methods disclosed herein also advantageously enable cryopreserved cells to substantially maintain functionality. For example, methods disclosed herein enable cells to substantially maintain viability post-cryopreservation such that the cells can directly be implanted at a target site of a patient after the cells/substrate are thawed. In some embodiments, the target implantation site comprises an anterior segment of the eye, or a posterior segment of the eye, or a combination thereof. For example, in several embodiments, the target site includes one or more of a subretinal space, a suprachoroidal space, an anterior chamber, vitreous humor, or another suitable intraocular space, or combinations thereof. In some embodiments, the methods disclosed herein enable direct implantation at a target site a cryopreserved substrate having a monolayer of fully differentiated hESC-RPE cells attached thereon. Additionally, methods disclosed herein further enable controlled production in bulk of cryopreserved cells seeded on a substrate that substantially maintain functionality or viability post-thaw such that the cells are suitable for direct implantation within a patient.

In several embodiments, stem cells are seeded on a substrate; cultured to a desired final density, washed, transferred to a cryovial containing freezing medium (e.g., CryoStem from Stemgen); and subject to controlled temperature reduction. Additionally, in some embodiments, the cells are differentiated in culture prior to cryopreservation. In some embodiments, the cells are cultured on a substrate comprising a polymer material or a non polymer material, or a combination thereof. In some embodiments, the substrate is a parylene. In several embodiments, the substrate is coated, in particular on a portion of the substrate designed for cell growth or attachment. For example, a cell-attachment surface of the substrate may be treated to promote cell adhesion onto the cell-attachment surface or to enhance viability of cells adhered to the cell-attachment surface. In several embodiments, the substrate is coated with MATRIGEL™ or other similar agents to promote cell attachment or support cell viability. In some embodiments, the substrate can be treated with a coating comprising vitronectin, retronectin, or combinations thereof. In other embodiments, the membrane is coated with a commercially available compound (e.g., CellStart (Invitrogen)). In several embodiments, the substrate seeded with stem cells is cultured in the presence of FGF (or other growth factor(s)) until the cells are confluent (or until they reach a desired confluence). In some embodiments, the substrate seeded with stem cells is cultured under conditions that promote the differentiation of the stem cells. In some embodiments, the substrate-adhered cells are cryopreserved in a serum and protein free freezing media. In some embodiments, the cell-seeded substrate is loaded into a cryovial (or other suitable vessel for freezing/storage) and then subjected to cryopreservation.

In some embodiments, cells are cooled in a temperature ramp-down phase having a selected rate of temperature reduction. In some embodiments, a rate of temperature reduction in a temperature ramp-down phase is about 10° C. per minute. In several embodiments, other rates of change are used, such as about 1° C. per minute, about 2° C. per minute, about 5° C. per minute, about 7° C. per minute, about 12° C. per minute, about 15° C. per minute, about 17° C. per minute, about 20° C. per minute, or rates within the values above. In several embodiments, a temperature ramp-down phase may include a flash freezing (e.g., maximal temperature reduction) step. For example, a flash freeze step may comprise a flash-freeze rate of temperature change having an increased rate of temperature reduction, where the rate is selected to advantageously improve cell integrity or cell viability. In contrast, in several embodiments and counter to conventional wisdom, a flash freeze step is not employed. Applicants have discovered, in certain embodiments, that maximal rates of temperature reduction are similarly damaging as certain slower rates of reduction, while certain intermediate rates provide an unexpectedly improved quality of cryopreservation and/or cell viability. In some embodiments, a temperature ramp-down phase may include cooling the substrate-adhered cells at a rate of approximately 10° C. per 10 seconds, 10° C. per 20 seconds, 10° C. per 30 seconds, 10° C. per 40 seconds, 10° C. per 50 seconds, 10° C. per 60 seconds, 10° C. per 70 seconds, 10° C. per 80 seconds, 10° C. per 90 seconds, 10° C. per 100 seconds, 10° C. per 110 seconds, 10° C. per 120 seconds, 10° C. per 130 seconds, 10° C. per 140 seconds, 10° C. per 150 seconds, 10° C. per 160 seconds, 10° C. per 170 seconds, 10° C. per 180 seconds, 10° C. per 190 seconds, or 10° C. per 200 seconds. A rate of cooling in a temperature ramp-down phase is configured to improve cell viability, in some embodiments. For example, certain cooling rates in a temperature ramp-down phase improves cell functionality post-cryopreservation. In some embodiments, cooling rates in a temperature ramp-down phase are configured to improve cell integrity or stability. In some embodiments, the cryopreserved cells substantially maintain therapeutic effect post-cryopreservation. For example, the cells are suitable for direct implantation at a target site of a patient post thawing of the cryopreserved cells with a yield of therapeutic efficacy roughly equivalent to (or better than) cells that have not been cryopreserved.

In some embodiments, substrate-adhered cells are optionally subjected to an intermediate storing temperature for a desired period of time. The intermediate storing temperature, in several embodiments, ranges from between about 0° C. and −100° C., including about −50° C. to about −60° C., about −60° C. to about −70° C., about −70° C. to about −80° C., about −80° C. to about −90° C., about −90° C. to about −100° C., and overlapping ranges thereof. In some embodiments, cells may be stored at an intermediate storing temperature for a pre-determined period of time before transfer to longer term storage. For example, the cells may be maintained at an intermediate storing temperature overnight, or any other suitable period of time, before being transferred to liquid nitrogen for long term storage. Other temperatures may be used in other embodiments (e.g., storage at −20° C., −30° C., −40° C., −50° C., −60° C., etc.) This interim storage serves as a temperature "step-down" that further enhances the stability, viability and function of the cells seeded on the substrate post-thaw. In several embodiments, a multi-step "step down" procedure is used.

In some embodiments cryopreserved substrate-adhered cells are thawed for use (e.g., implantation) by transferring a cryovial containing the cryopreserved substrate-adhered cells to a water bath having a temperature around body temperature, for example a temperature of around 37° C., or any other suitable temperature. In other embodiments, a "step up" thawing process having a step up heating rate is used. For example, the cryovial may, in some embodiments, be placed in sequential storage environments with increasing temperatures before being transferred to a temperature that is around body temperature, for example a water bath having a temperature of around 37° C., or any other suitable temperature. In several embodiments, the final incubator is located in the operating room, allowing a surgeon to immediately select and implant a cell-seeded substrate. In several embodiments, after thawing the substrate-adhered cells may be transferred to a culture dish and cultured under appropriate conditions for a period of approximately 30 minutes, one hour, 6 hours, 12 hours, 24 hours, 48 hours, 72 hours, 86 hours, 110 hours, one week, two weeks, or more than three weeks prior to being transported to the desired location (e.g., the operating room for delivery to a patient). In some embodiments, the substrate-adhered cells medium supplemented with FGF2. Alternatively, in several embodiments, the thawed cell-seeded substrate is directly implanted into a patient.

Examples provided below are intended to be non-limiting embodiments of the invention. It shall be appreciated that equivalent or alternative reagents or alternative concentrations, incubations times/temperatures are within the scope of the present disclosure.

Example 1

Two hours prior to disassociation from a culture vessel, the culture medium of stock H9-RPE cells was changed to fresh X-VIVO 10 medium. The differentiated H9-RPE cells were then washed with calcium-free and magnesium-free DPBS (Mediatech, Inc., Va.), pH7.4, once and dissociated with 0.05% trypsin with 0.53 mM EDTA (Mediatech, Inc., Va.) for 5 minutes at 37° C. The cells were then thoroughly dissociated by pumping the trypsin-EDTA solution up and down gently over the cells with a pipette (culture plate or dishes) or by transferring the cells by pipette to a culture flask. The trypsin was then neutralized with equal volume of X-VIVO 10 medium (Lozan) containing 10% FBS (Hyclone or other xeno-free neutralization reagents). The cell suspensions were filtered through a sterile 40 μm strainer to remove non-disassociated cells and the disassociated cells were pelleted with a Hirmle Z 300 centrifuge (RPI Corp., Ill.) and centrifuged at 1000 rpm for 5 minutes.

The cell pellets were then washed with X-VIVO 10 medium twice, and counted with a hemocytometer. Cells were seeded on either CELLSTART (Invitrogen) or MATRIGEL (BD Biosciences) coated parylene membranes or other polymeric membranes at the density of $10^5/cm^2$ in X-VIVO 10 medium supplemented with 10 ng/ml FGF2 (R&D Systems). The cells were cultured on the membranes in X-VIVO 10 medium with FGF for one week, then in X-VIVO 10 medium without FGF supplementation for three more weeks. The media was changed twice a week.

The seeded cells grew to confluence after one week in culture. After two week culture, the cells started to form RPE typical morphology, taking on a cobblestone shape and pigmentation.

After 4 weeks culture, the fully differentiated RPE cells grown on the substrate membrane were washed with X-VIVO 10 medium once and then transferred to a cryovial containing 1 ml of CryoStem freezing medium (Stemgen). The cryovials that contained cells with freezing medium were placed in a COOLCELL® container (BioCision). The temperature of the cells was lowered at a rate of 10° C. per minute, to a final temperature of approximately 0° C. The substrate-adhered cells were then stored in a –80° C. freezer overnight. The frozen cryovials were then transferred into a CRYOBOX™ (Thermo Fisher Scientific) and stored in liquid nitrogen.

Figure 1:
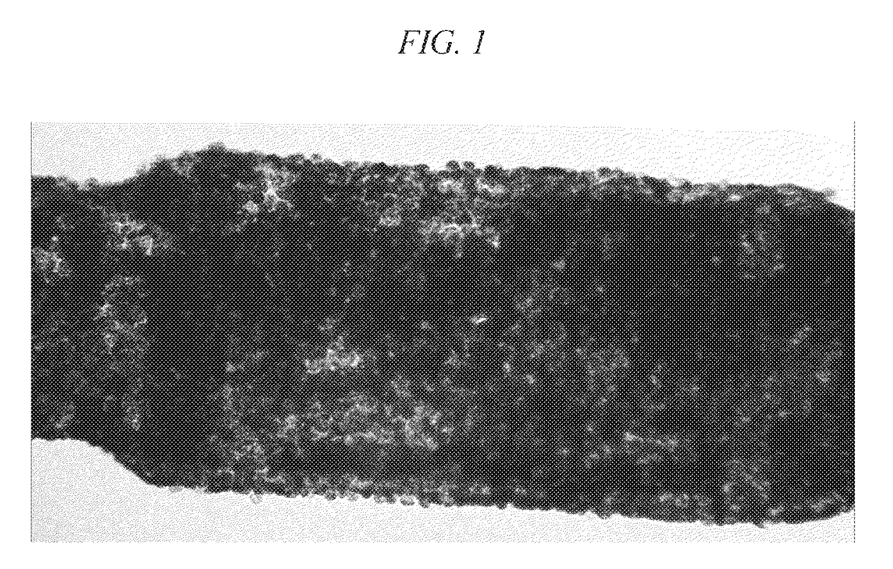
FIG. 1 depicts hESC-RPE grown on a parylene substrate after a freeze-thaw cycle.
Figure 2:
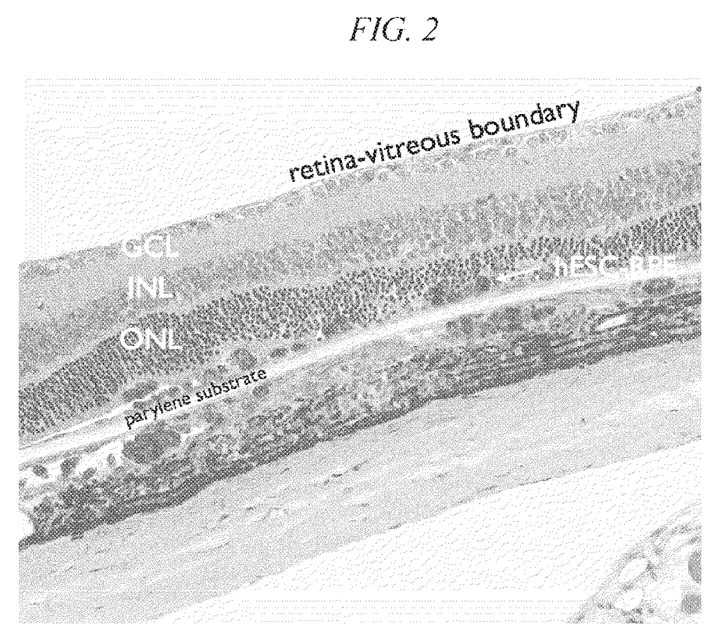
FIG. 2 depicts histology of a rat eye one week after transplantation of a cryopreserved parylene substrate seeded with hESC-RPE. The cells are both viable and functional, as shown by the polarized monolayer of RPE formed.
Figure 3A:
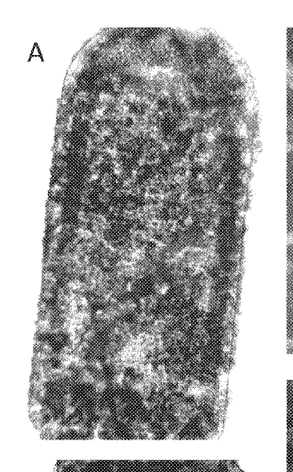
FIG. 3A shows a cell-seeded substrate previously cryopreserved) 1 day post-thaw.
Figure 3B:
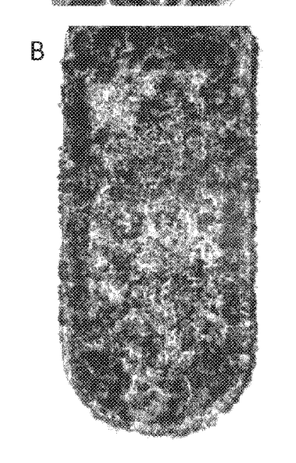
FIG. 3B shows a cell-seeded substrate previously cryopreserved) 1 day post-thaw.
Figure 3C:
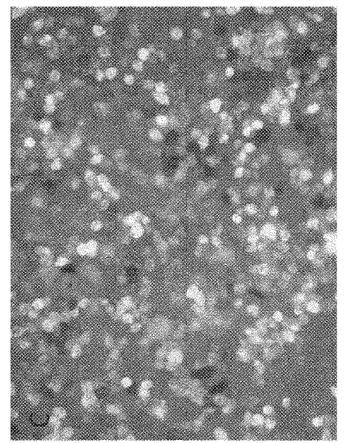
FIGS. 3C-3F depict in vitro cell viability analysis from 4 representative areas of a 1 day post-thaw substrate.
Figure 3D:
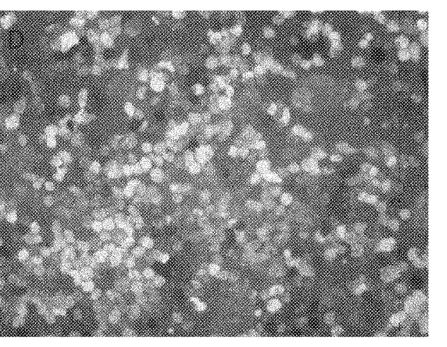
Figure 3E:
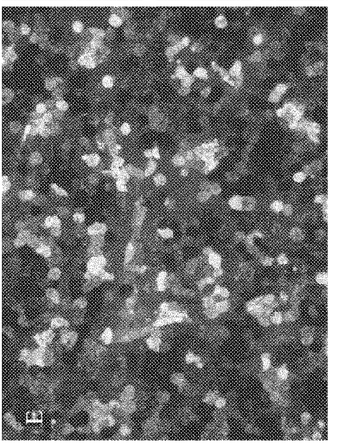
Figure 3F:
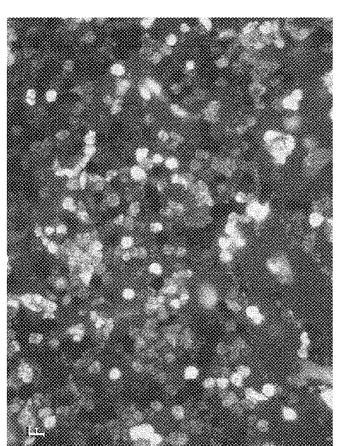

As discussed above, in several embodiments, cryovials containing RPE cells on the substrate are thawed for implantation in a patient. The cryopreserved implants were taken out from liquid nitrogen container and immediately placed in a 37° C. water bath (or other equivalent environment). After thawing, the RPE cell-seeded substrates were carefully transferred from the cryovial into 35-mm tissue culture dishes and washed twice in 3 ml X-VIVO 10 medium and transferred into culture wells of a 24-well plate and cultured in X-VIVO 10 medium supplemented with 10 ng/ml FGF2. The cells were cultured for a week with medium changed every other day. After one week recovering in X-VIVO 10 with FGF supplement, the cells with substrate membrane were ready to transplant into animal or could be continuously cultured in X-VIVO 10 medium without FGF2 supplement. In other embodiments, no post-thaw culturing is required (e.g., implantation can be performed as soon as thawing is completed). As shown in FIG. 1, post "freeze and thaw", the RPE cells remain attached to the parylene substrate and have intact monolayers (e.g., RPE tight-junctions are not compromised due to change in temperature). Also, as shown in FIGS. 3A-3B, there is limited cell loss post-thaw at 1 day (3A) and 1 week (3B). Additionally, not only do the cells remain on the substrate, but they remain viable post-thaw as well. FIGS. 3C-3F depict cell viability analyses that demonstrate that the percentage of living cells post-thaw is substantially greater than dead cells (3C-3F represent 4 different fields of view). Moreover, 1-week post-implantation into the rat sub-retinal space, histological analysis showed that the previously cryo-preserved RPE cells on the substrate membrane not only survive, but retain functionality as evidenced by their formation and maintenance in vivo of a polarized monolayer (FIG. 2).

What is claimed is:

1. A method of cryopreserving a monolayer of seeded cells, stem cells, stem cell derived cells, or combinations thereof on a substrate, the method comprising:
   exposing a substrate seeded with a monolayer of cells to a temperature ramp-down phase temperature reduction rate between 10° C. per 10 seconds to 10° C. per 120 seconds to a final temperature of approximately 0° C.,
   wherein the substrate comprises parylene,
   wherein the substrate has one or more characteristics selected from
      (i) a coefficient of thermal expansion of the substrate,
      (ii) a substrate elasticity parameter, or
      (iii) a substrate thickness, said characteristics enhancing viability of the seeded cells;
   transferring the cell-seeded substrate to an intermediate temperature between –20° C. and –100° C. for a first period of time; and,
   maintaining the cells at a storage temperature that is lower than the intermediate temperature for a second period of time, thereby obtaining cryopreserved cells.

2. The method of claim 1, wherein said first period of time is between 6 and 48 hours.

3. The method of claim 1, wherein said storage temperature is achieved using liquid nitrogen.

4. The method of claim 1, wherein the substrate further comprises a coating to enhance adhesion of the cells to the substrate, wherein the coating comprises one or more of MATRIGEL® biological cell culture substrate, vitronectin, and RETRONECTIN® reagent, and wherein said coating enhances the viability of the cells during cryopreservation, after cryopreservation, or both.

5. The method of claim 1, wherein said parylene is parylene C.

6. The method of claim 1, wherein the seeded cells comprise human embryonic stem cell-retinal pigment epithelium (hESC-RPE) cells.

7. The method of claim 6, wherein the seeded cells comprise a monolayer of fully differentiated hESC-RPE cells.

8. The method of claim 1, wherein the parylene substrate is non-porous and permeable.

9. The method of claim 1, further comprising thawing the cryopreserved cells on said substrate by a method comprising:
   warming the cell-seeded substrate to a target temperature using a temperature ramp-up heating rate to obtain thawed cells seeded on the substrate, wherein the thawed cells retain viability and/or functionality post-thaw.

10. The method of claim 9, wherein the thawed cells are cultured in a media comprising one or more of a fibroblast growth factor (FGF) and an FGF supplement.

11. The method of claim 9, wherein the thawed cells are cultured in a media without growth supplements.

12. The method of claim 1, wherein the temperature ramp-down phase comprises a temperature reduction rate that is within a range of 7° C. per minute to 17° C. per minute.

* * * * *